United States Patent [19]

Burd et al.

[11] Patent Number: 5,470,752

[45] Date of Patent: Nov. 28, 1995

[54] MULTI-LAYER DEVICES AND METHODS OF ASSAYING FOR FRUCTOSAMINE

[75] Inventors: John F. Burd; Talei Hoblitzell, both of San Diego; Gebhard Neyer, Los Angeles, all of Calif.

[73] Assignee: LXN Corporation, Irvine, Calif.

[21] Appl. No.: 269,351

[22] Filed: Jun. 29, 1994

[51] Int. Cl.[6] .................................................. G01M 33/52
[52] U.S. Cl. .................. 436/87; 436/169; 436/178; 436/825; 435/4; 435/805; 422/56; 422/82.09
[58] Field of Search ................................. 422/55, 56, 57, 422/58, 87.05, 82.09; 436/87, 169, 178, 805, 825; 435/4, 805

[56] References Cited

U.S. PATENT DOCUMENTS

| | | | |
|---|---|---|---|
| 3,552,929 | 1/1971 | Fields et al. | 23/253 |
| 3,802,842 | 4/1974 | Lange et al. | 23/253 |
| 3,809,605 | 5/1974 | Schmitt et al. | 162/158 |
| 3,897,214 | 7/1975 | Lange et al. | 23/253 |
| 4,042,335 | 8/1977 | Clement | 23/253 |
| 4,050,898 | 9/1977 | Goffe, et al. | 23/253 |
| 4,642,295 | 2/1987 | Baker | 436/87 |
| 4,645,742 | 2/1987 | Baker | 436/15 |
| 4,935,346 | 6/1990 | Phillips et al. | 435/14 |
| 4,956,301 | 9/1990 | Ismail et al. | 436/87 |
| 5,002,893 | 3/1991 | Rosenthal | 436/87 |
| 5,049,487 | 9/1991 | Phillips | 435/4 |
| 5,059,394 | 10/1991 | Phillips et al. | 422/68.1 |
| 5,169,787 | 12/1992 | Knappe et al. | 436/169 |
| 5,258,163 | 11/1993 | Krause et al. | 422/58 |
| 5,271,895 | 12/1993 | McCrosky et al. | 422/58 |

FOREIGN PATENT DOCUMENTS 0388782  9/1990  European Pat. Off. .
0473189A2  3/1992  European Pat. Off. .

OTHER PUBLICATIONS

Johnson et al., "Fructosamine: a new approach to the estimation of serum glycosylprotein. An index of diabetic control." *Clinica Chimica Acta,* 127:87–95 (1982).

Caines et al., "Colorimetric determination of non-enzymatically glycated albumin." *Clinical Biochemistry,* 19:26–30 (Feb. 1986).

David A. Armbruster, "Diabetes mellitus, protein glycation, and laboratory assays for monitoring long-term glycemic control." *Clinical Laboratory Science,* 3(3):184–188 (1990).

David A. Armbruster, "Fructosamine: Structure, Analysis, and Clinical Usefulness." *Clinical Chemistry,* 33 (12):2153–2163 (1987).

*Primary Examiner*—David A. Redding
*Attorney, Agent, or Firm*—Campbell and Flores

[57] ABSTRACT

The present invention is directed to a multi-layer test device and method for analyzing the concentration of fructosamine in a liquid sample. The multi-layer test device has a buffer layer containing a buffer having a pH value of at least 9 which is either superposed above or juxtaposed to an indicator layer containing an indicator capable of being reduced by fructosamine. Supporting the buffer layer, the indicator layer, and any additional layers in the multi-layer device is at least one support member which optionally has a detection aperture for analyzing the concentration of fructosamine on the indicator layer. An additional support member having a sample aperture can be used. Where two support members are used the multi-layers are sandwiched between the first support member having a sample aperture and the second support member optionally having a detection aperture.

25 Claims, 5 Drawing Sheets

FIG. 5 ns sandwich the juxtaposed multi-layers.

MULTI-LAYER DEVICES AND METHODS OF ASSAYING FOR FRUCTOSAMINE

BACKGROUND OF THE INVENTION

Field of the Invention

The present invention relates to a multi-layer test device, and more specifically, to analyzing a liquid sample for the concentration of fructosamine.

Background Information

Individuals suffering from diabetes mellitus have an abnormally high blood sugar level because the pancreas does not secrete sufficient amounts of the active hormone insulin into the bloodstream to regulate carbohydrate metabolism. If an abnormally high blood sugar level, known as a hyperglycemic condition, is allowed to continue for prolonged periods, the individual will suffer from the chronic complications of diabetes, including retinopathy, nephropathy, neuropathy and atherosclerosis.

It is known that proteins, such as those present in blood serum and other biological fluids, react with glucose, under non-enzymatic conditions, to produce glycated proteins, also known as fructosamines or ketoamines. The extent of the reaction is directly dependent upon the glucose concentration of the blood. Consequently, diabetics usually have an elevated fructosamine concentration compared to a healthy individual. Therefore, the concentration of glycated serum proteins has been used as an indicator of a hyperglycemic condition. To assist in the detection, monitoring and treatment of diabetes, blood sugar concentrations can be determined indirectly by analyzing for fructosamine. In particular, measurement of fructosamine levels is useful for monitoring diabetic control because fructosamine concentration reflects an average of serum glucose levels over a period of time, approximately a half month period.

Fructosamines are formed as follows. The blood proteins are glycated in vivo by a non-enzymatic reaction between glucose and available amino groups of blood proteins. The glucose binds to an amino group of the protein to form a Schiff base, i.e., an aldimine, that undergoes molecular rearrangement to form a stable ketoamine. In the art, such ketoamines are generically known as "fructosamines." The degree of protein glycation and fructosamine formation is directly proportional to blood glucose concentration.

Many of the existing methods for determining the degree of diabetic control are unreliable. For example, tests which directly measure plasma glucose have been found to be inadequate or even misleading because blood glucose levels fluctuate significantly throughout a given day, being influenced by diet, activity, and treatment.

Because of the shortcomings of direct glucose measurements, tests which are long term indicators of blood glucose levels were developed. One of the first such tests measured glycated hemoglobin. Because of the expense, requirement for trained technicians and lack of reproducibility associated with measuring glycated hemoglobin, more reliable tests of measuring for serum fructosamine developed. An assay for fructosamine overcomes some of the disadvantages of the assay for glycated hemoglobin because fructosamine measurements are technically simpler to perform and reflect a shorter time period of glycemic control (½ month) compared to glycated hemoglobin (2 to 3 months).

Baker, in U.S. Pat. Nos. 4,642,295 and 4,645,742, discloses methods for determining fructosamine levels. The disclosed methods however use a solution assay, which has several practical limitations, such as inconvenience associated with solution assays and the need for relatively large volumes of liquid sample. Such methods have been adapted to dry-phase chemistry, for example by Ismail, as disclosed in U.S. Pat. No. 4,956,301. However, Ismail's dry-phase assay is a test-strip device, which requires the use of a reaction accelerator compound and which is incapable of performing with certain reagents which are especially useful in fructosamine assays, namely Nitroblue tetrazolium chloride (NBT) and carbonate buffer.

Multi-layer test devices are generally known in the art. Many patents in the field, such as Goffe et al. U.S. Pat. No. 4,050,898, however, describe the need for a spreading layer. To overcome the use of spreading layers some multi-layer devices have an air gap between the first support member and the multi-layer analysis film, as shown in the published European Patent Application 0 388 782.

Sakamoto, in the published European Patent Application 0 473 189, describes a multi-layer analytical element for assaying fructosamine. The arrangement of the multi-layers, as well as the materials used, however, are different than the instant invention. As a result, Sakamoto's element requires the use of binders and is incapable of analyzing fructosamine levels in whole blood.

Therefore, a need still exists in the art for a simple dry-phase test device which involves only the minimal chemistry required for analyzing the concentration of fructosamine. And in particular, a need still exists for adopting this chemistry to a simple multi-layer test device which does not require a spreading layer or air gap and which can analyze the concentration of fructosamine in whole blood. The present invention satisfies these needs and provides related advantages as well.

SUMMARY OF THE INVENTION

The present invention is directed to a new multi-layer test device and method for analyzing the concentration of fructosamine in a liquid sample. The simple yet accurate multi-layer test device has a buffer layer containing a buffer having a pH value of at least 9 which is either superposed above, or juxtaposed to, an indicator layer containing an indicator capable of being reduced by fructosamine. Supporting the buffer layer, the indicator layer and any additional layers in the multi-layer device, is at least one support member which optionally has a detection aperture for analyzing the concentration of fructosamine. An additional support member having a sample aperture can be used. Where two support members are used, the multi-layers are sandwiched between the first support member having a sample aperture and the second support member optionally having a detection aperture.

DETAILED DESCRIPTION OF THE INVENTION

The present invention provides a simple, yet accurate, multi-layer test device and method for analyzing the concentration of fructosamine in a liquid sample. The invention provides distinct advantages over other dry phase test devices in the fructosamine art. Surprisingly and unexpectedly, the instant invention can analyze any type of liquid sample, including whole blood, at ambient temperature without using a reaction accelerator. Further, spreading layers or air gaps are not required for accurate measurements of fructosamine.

In general, the fructosamine concentration in the blood reflects an average glucose concentration in the blood over a period of time, approximately a half month period. Since fructosamine formation is directly dependent upon glucose concentration, diabetic individuals have higher fructosamine concentrations in the blood as compared to unaffected individuals. Under alkaline conditions, the fructosamines that form in the blood are converted to eneaminols. The eneaminol form of fructosamine is a chemically active reducing substance that reacts with a suitable indicator capable of being reduced by fructosamine. For example, the color transition of a chromogenic dye or the fluorescence of a fluorescent reagent resulting from this reaction can be measured and compared with a standard to give an indication of the average glucose concentration in blood samples over the prior half month period. This correlation to glucose concentration is possible even though the glucose remains associated with the protein in the blood and has undergone a molecular rearrangement to form a fructosamine.

The liquid sample to be analyzed for fructosamine concentration can be a naturally occurring or an artificially formed liquid suspected to contain fructosamine, and is usually a biological liquid sample, or dilution thereof. The biological liquid sample from which fructosamine concentration can be determined include whole blood, serum, plasma, urine, and saliva. The present invention is especially useful for analyzing fructosamine found in whole blood which is not possible with other prior art multi-layer devices.

The analysis for fructosamine with the invention can be done at ambient or room temperature (approximately 30° C.). The prior art either uses reaction accelerators or elevated temperatures. Ismail's dry-phase assay described in U.S. Pat. No. 4,956,301, requires the use of a reaction accelerator compound to analyze fructosamine levels at ambient temperature. Sakamoto's multi-layer analytical element described in published European Patent Application 0 473 109 requires elevated temperatures on the order of 40° C. Surprisingly, and unexpectedly, with the instant multi-layer test device neither additional compounds for reaction acceleration nor elevated temperatures are required.

The Multi-Layers

Figure 1A:
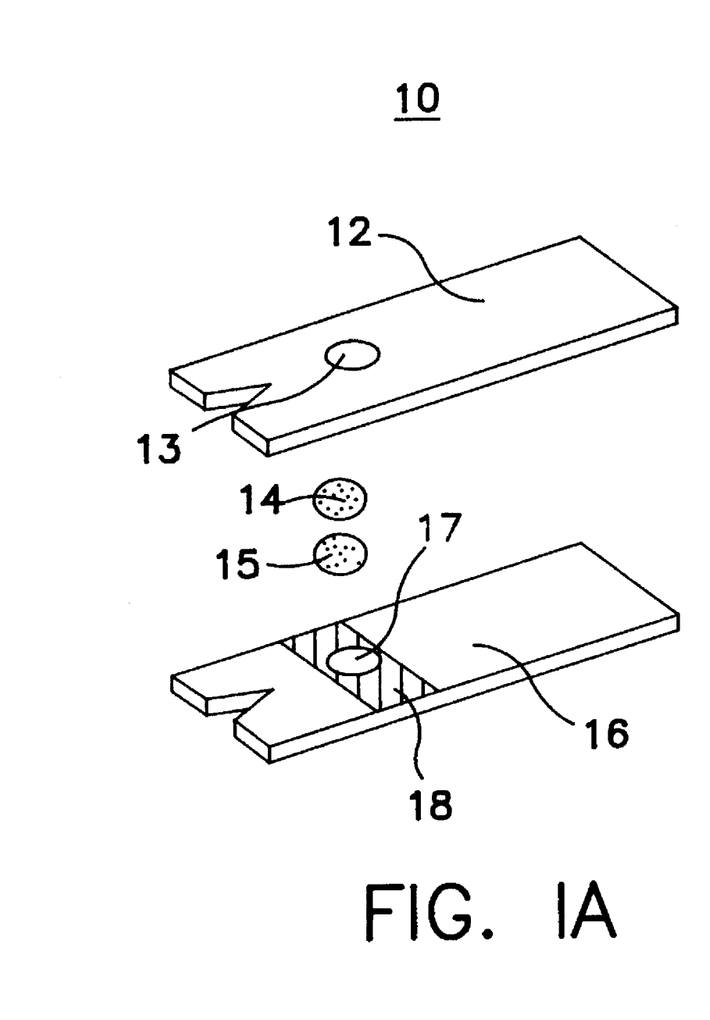
FIG. 1a is a schematic of a two support member, multi-layer test device which exemplifies the buffer layer superposed above the indicator layer.
Figure 1B:
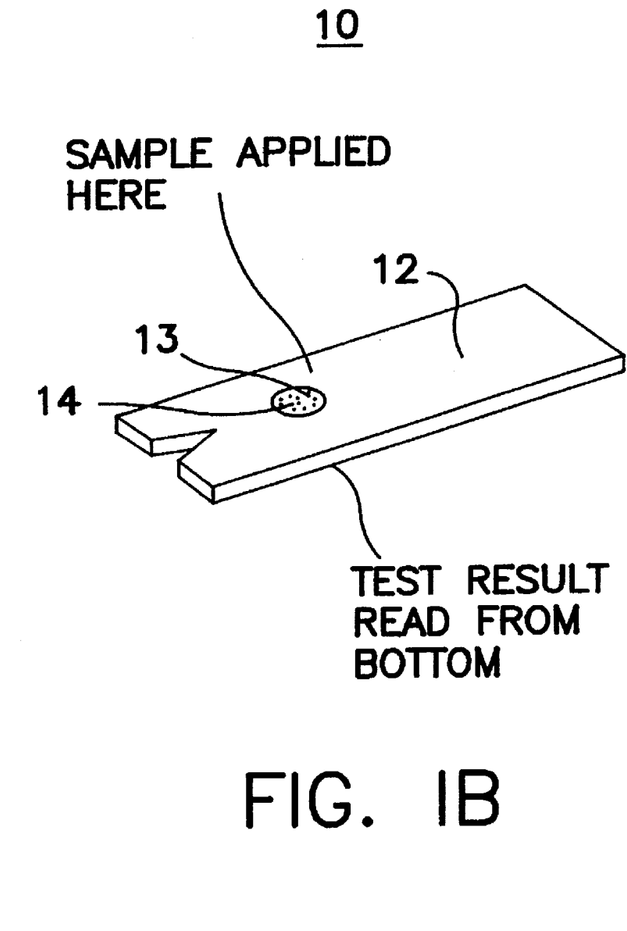
FIG. 1b is a schematic of the two support member, multi-layer test device of FIG. 1a, wherein the two support members sandwich the superposed multi-layers.
Figure 2A:
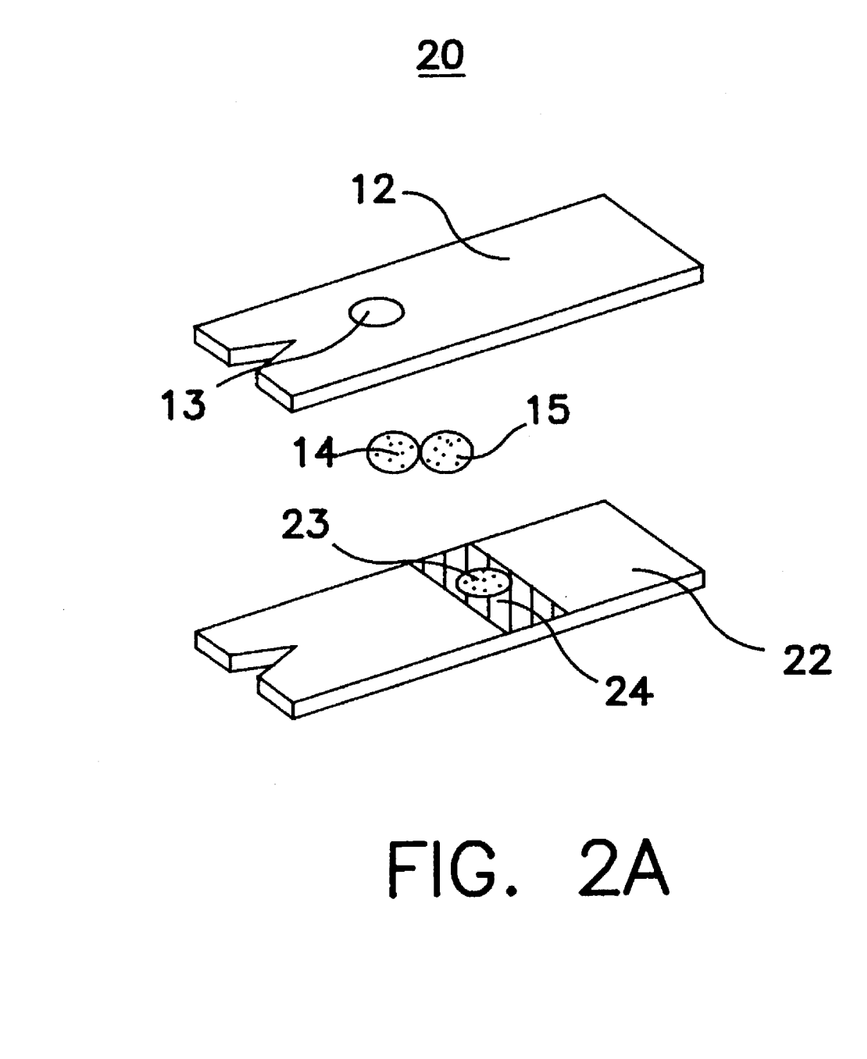
FIG. 2a is a schematic of a two support member, multi-layer test device which exemplifies the multi-layers juxtaposed relative to one another.
Figure 2B:
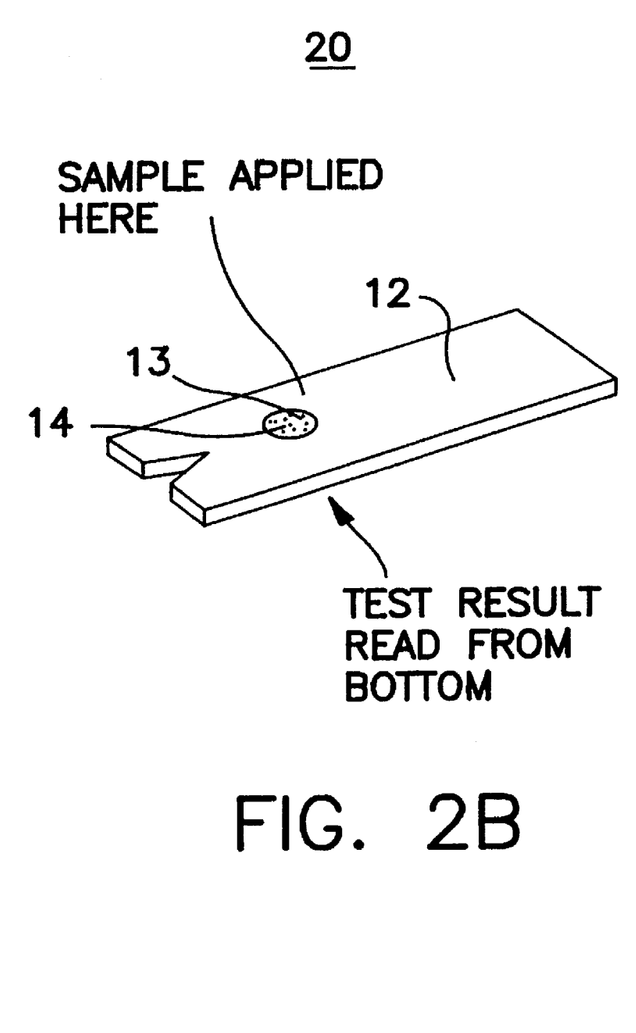
FIG. 2b is a schematic of the two support member, multi-layer test device of FIG. 2a, wherein the two support members sandwich the juxtaposed multi-layers.
Figure 3A:
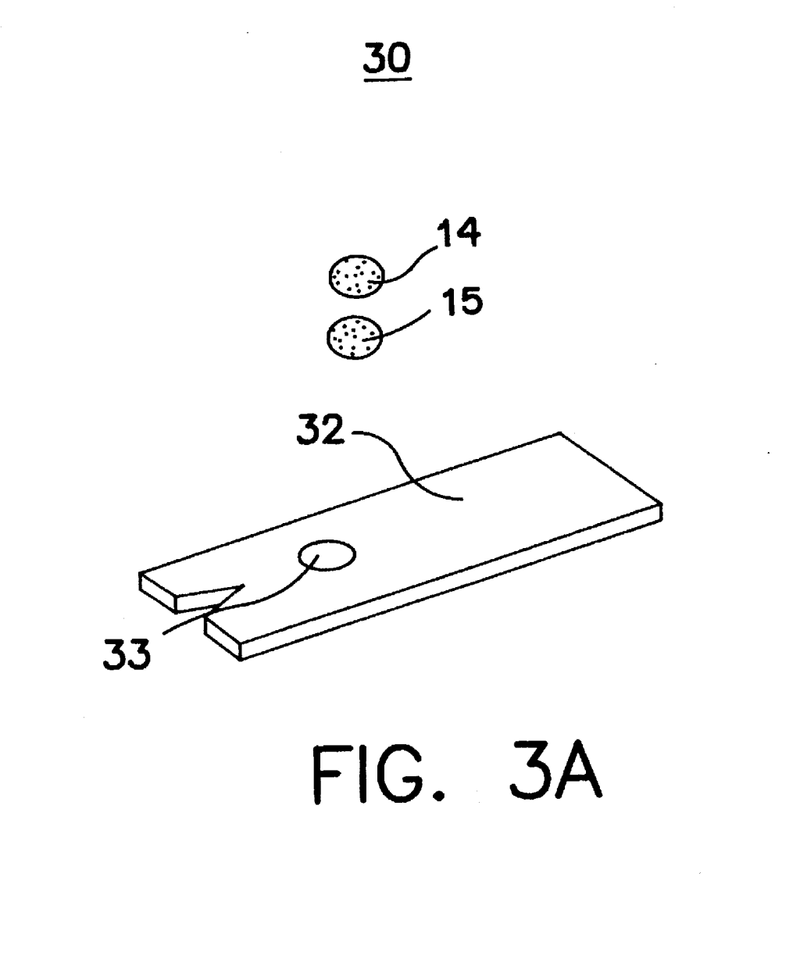
FIG. 3a is a schematic of a one support member, multi-layer test device which exemplifies the buffer layer superposed above the dye layer.
Figure 3B:
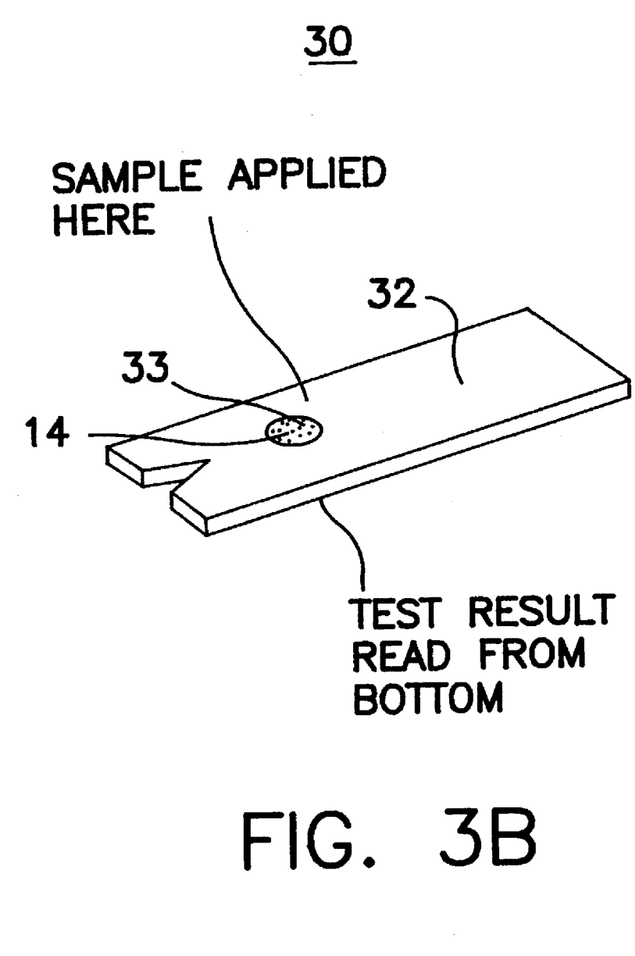
FIG. 3b is a schematic of the one support member, multi-layer device of FIG. 3a, wherein the buffer layer is superposed above the dye layer on the support.
Figure 4A:
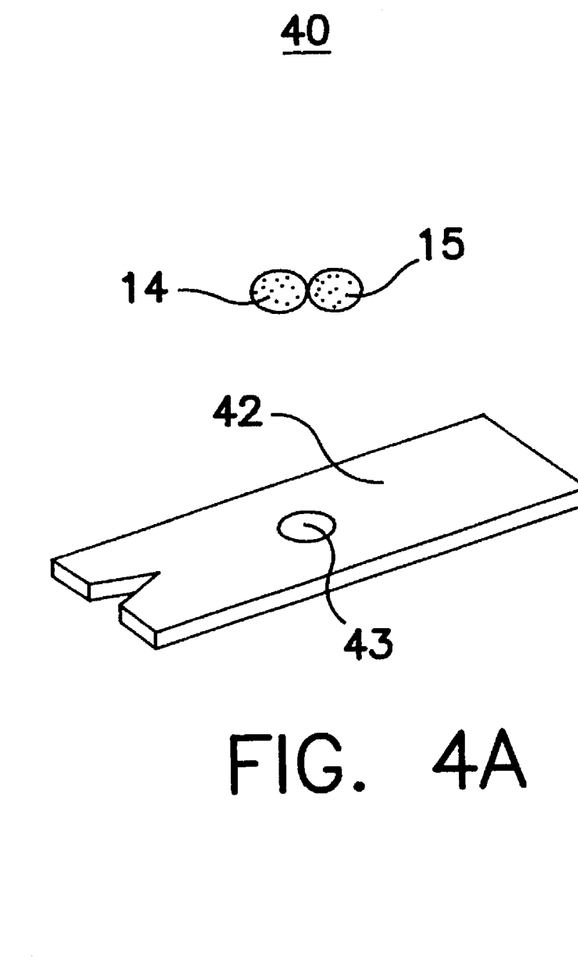
FIG. 4a is a schematic of the one support member, multi-layer test device which exemplifies the multi-layers juxtaposed relative to one another.
Figure 4B:
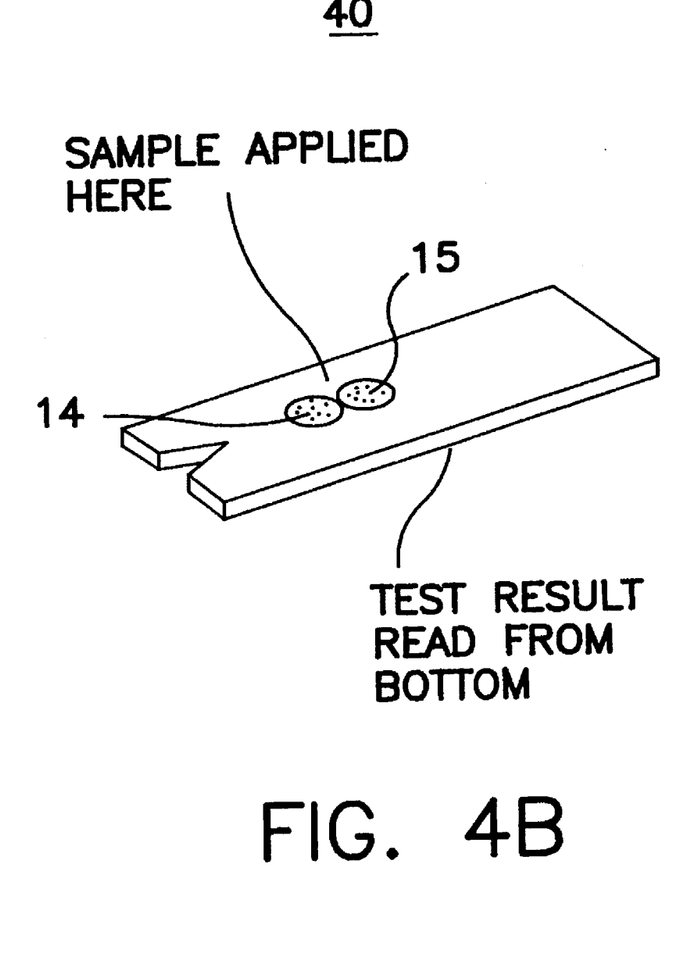
FIG. 4b is a schematic of the one support member, multi-layer device of FIG. 4a, wherein the multi-layers are juxtaposed on the support.

According to the instant invention the layers of the multi-layer test device are positioned adjacent to each other so that they provide for fluid communication. The fluid flow between the adjacent layers can be either vertical or lateral. Accordingly, the layers of the multi-layer device can be superposed (as shown in FIGS. 1 and 3) or juxtaposed (as shown in FIGS. 2 and 4).

The various multi-layers of the test device contain the assay reagents of interest, such as a buffer or an indicator. The reagent of interest may be impregnated into the layer or coated into or onto a layer or covalently attached to the layer.

The material for the various layers described herein, including the buffer layer, the indicator layer, and any additional layers, comprise a porous matrix which is capable of containing the assay reagent of interest but which is permeable to the fructosamine analyte and other critical assay realtents and liquids. The permeability generally arises from porosity, ability to swell or any other characteristic. The test device layers can comprise various porous, fibrous materials such as cellulose, papers, fleeces, felts, woven fabric and the like (see, for example, U.S. Pat. Nos. 3,802,842; 3,809,605; and 3,897,214, all of which are incorporated herein by reference). Alternatively, the test device layers can comprise porous, non-fibrous materials, such as microporous polymers (see, for example, U.S. Pat. No. 3,552,929, which is incorporated herein by reference). Specific examples of suitable materials which can be used for the layers include filter paper, such as 3 mm filter paper, Rayon, Cytosep® membrane (Ahlstrom Filtration, Inc., Mt. Holly Spring, Pa.), glass fiber, and Biodyne A nylon membrane.

According to the present invention, the multiple layers containing the assay reagents, such as buffer or indicator, can be assembled simultaneously or sequentially. The porous material for a given layer is first placed in a solution of assay reagent such as a buffer solution or an indicator solution. After drying, the layer can be stored in a desiccator cabinet until it is ready for use in the multi-layer test device.

The multi-layers are generally in the form of reagent pads which are mounted onto one support member or sandwiched between two support members as discussed more fully below. The multi-layer pads can be any geometrical dimension, such as circular or rectangular, and are generally 0.5 to 20 mm in circumference, preferably 1 to 10 mm, and are positioned either superposed or juxtaposed relative to each other.

Regardless of the multi-layer positioning, the test devices embodied by the present invention comprise the basic elements of a buffer layer, an indicator layer and can contain additional layers as described below.

Buffer Layer

The buffer layer 14 contains a buffer having a pH value of at least 9. Various known types of buffers can be contained in the buffer layer as long as the buffer provides sufficiently high pH such that the fructosamines are converted to their eneaminol form. To achieve this, the pH of the buffer should be at a pH value between about 9 and about 13, and for optimum results the pH is at a pH value of between 10 and 12. Examples of such buffers include potassium hydrogen phosphate, sodium hydrogen phosphate, sodium hydroxide, guanidinium salts, certain amino acids, and other suitable buffers as are well known in the art, or combinations thereof. Where the buffer layer is superposed above the indicator layer it is generally of a non-opaque material.

Indicator Layer

The indicator layer 15 contains any indicator capable of being reduced by fructosamine such as certain dyes, including chromogenic dyes, or fluorescent reagents. Examples of suitable chromogenic dyes which change color based on the amount of fructosamine present in a liquid sample include tetrazolium dyes such as Neotetrazolium chloride (NT), Tetranitroblue tetrazolium chloride (TNBT), Blue tetrazolium chloride (BT), Iodonitrotetrazoilum chloride, Nitroblue tetrazolium chloride (NBT), Nitro Blue Monotetrazolium Chloride, Thiazolyl blue tetrazolium bromide (MTT), Tetrazolium violet, 2,3,5-Triphenyl-2-H-tetrazolium chloride, Thiocarbamyl nitro blue tetrazolium chloride (TCNBT), Tetrazolium XTT (XTT), 2-2'-Benzothiazolyl-5-styryl-3-(4'-phthalhydrazidyl)tetrazolium chloride (BSPT), Distyryl nitroblue tetrazolium chloride (DSNBT). An example of a suitable fluorescent reagent is 5-Cyano-2,3-ditolyl tetrazolium chloride (CTC).

Additional Layers

In the instant invention other layers, in addition to the buffer layer and the indicator layer, can be used in accordance with the instant invention. For example, the multi-layer test devices can include a red blood cell (RBC) separation layer before the buffer layer pad, for the purpose of separating RBC components. Other useful layers, include, but are not limited to, those described in U.S. Pat. Nos. 4,050,898 and 4,042,335, which are incorporated herein by reference, including radiation blocking layers, interference removal layers which may contain detergents, chelators, anti-oxidants, or other substances which can interfere with accurate results, contamination prevention layers, dialysis layers, filtering layers, support layers and the like.

Supporting the Multi-Layers

The support member or members in the instant invention can be opaque, reflective, or transparent to light or other energy. The support member(s) will be compatible with the intended analysis mode and indicator used (such as chromogenic or fluorescence indicators). Materials that can be used for the support members include a variety of plastics and polymers such as cellulose acetate, polyester, polycarbonate, polyvinylchloride, polyethylene, and polystyrene. Generally, where such materials are used, the support member is substantially planar. The layers can also be housed in a plastic container which holds layers in their proper orientation or they can be housed in other supports known in the art, such as the ICON device (Hybritech, Inc., San Diego, Calif.).

One Support Member Device

The instant invention has at least one support member optionally having a detection aperture. As used herein the phrase "optionally having a detection aperture" means that where the one support member is transparent, there is no need for a detection aperture whereas with a non-transparent support member a detection aperture is needed and present.

The detection aperture is a hole for observing the color transition or fluorescence on the indicator layer. The size of the aperture is smaller than the size of the multi-layers and its size depends on the size of the layer or layer pads. The aperture size will generally be from 0.5 to 20 mm, preferably between 1 and 10 mm. The position of the detection aperture on the bottom support member depends upon whether the multi-layers are superposed or juxtaposed (as shown for example in FIG. 1 versus FIG. 2). Where the multi-layers are superposed, the detection aperture is below all of the multi-layers (see for example FIG. 1). Where the multi-layers are juxtaposed, the detection aperture is directly below only the indicator layer or other final layer (see for example FIG. 2).

Where only one support is used, the liquid sample can be applied directly to the first multi-layer for example by a finger stick, pipet, dropper, or by dipping the device into the sample. The liquid sample freely permeates and diffuses into and flows through the buffer layer, and any additional layer present, and migrates to the indicator layer such that the concentration of fructosamine can be analyzed. The fructosamine concentration can be analyzed by visually or instrumentally examining a change in the indicator, such as determining the intensity or degree of color change in a chromogenic dye or the fluorescence in a fluorescent reagent. Fructosamine levels can be determined by use of an appropriate instrument, such as a spectrophotometer, including a reflectometer and fluorometer.

Two Support Member Device

While the invention can be carried out using only one support as described above, additional supports can be used. Where two supports are used, the multi-layers are sandwiched between a first support member having a sample aperture and a second support member optionally having a detection aperture. Like the detection aperture, the sample aperture is of a size less than the size of the multi-layers and its size depends to a large extent on the size of the layer or layer pads. The aperture size will generally be from 0.5 to 20 mm, preferably between 1 and 10 mm.

The two supports are held together by a securing means, such as adhesive. Examples of adhesive that can be used include gelatin, rubber, silicone, and acrylate base glue. In addition, the plastic housing may be sonically welded or snapped together as is common in the state of the art.

In using the two support member test devices, a drop of liquid sample is applied at the sample aperture to the first multi-layer pad, for example, by use of a finger stick, dropper, piper, or by dipping the device into the sample. The liquid sample freely permeates and diffuses into and through the buffer layer and any additional layer present, and migrates to the indicator layer such that the concentration of fructosamine can be analyzed. The fructosamine concentration can be analyzed by visually or instrumentally examining a change in the indicator, such as determining the intensity or degree of color change in a chromogenic dye or the fluorescence in a fluorescent reagent. Fructosamine levels can be determined by use of an appropriate instrument, such as a spectrophotometer, including a reflectometer and fluorometer.

The alternative embodiments of the invention will now be described with reference to the above-mentioned drawings. Referring to FIGS. 1a and 1b, in a preferred embodiment, the multi-layer test device 10 for analyzing the concentration of fructosamine in a liquid sample has two support members, a first substantially planar support member 12 having a sample aperture 13 and a second substantially planar support member 16 having a detection aperture 17. The two supports are held together by a securing means 18, such as an adhesive. Superposed and sandwiched between the two supports are the multi-layers, which include at least a buffer layer pad 14 and an indicator layer pad 15 wherein the buffer layer 14 is superposed in fluid communication above the indicator layer 15.

Referring to FIGS. 2a and 2b, in an alternative embodiment the multi-layer test device 20 is identical to the one described above, with the exception that the multi-layers are juxtaposed and the detection aperture 23 is positioned accordingly. This embodiment of the multi-layer test device 20 for analyzing the concentration of fructosamine in a liquid sample has two substantially planar support members, a first substantially planar support member 12 having a sample aperture 13 and a second substantially planar support member 22 having a detection aperture 23. The two supports are held together by a securing means 24, such as an adhesive. Juxtaposed in fluid communication and sandwiched between the two supports are the multi-layers, which include at least a buffer layer pad 14 and an indicator layer pad 15.

Referring to FIGS. 3a and 3b, in yet another alternative embodiment the multi-layer test device 30 has only one substantially planar support member. This embodiment of the multi-layer test device 30 for analyzing the concentration of fructosamine in a liquid sample has one substantially planar support member 32 with a detection aperture 33 which supports a buffer layer 14 superposed in fluid communication above an indicator layer pad 15.

Referring to FIGS. 4a and 4b, in still another alternative embodiment the multi-layer test device 40 is identical to the embodiment described above with the exception that the multi-layers are juxtaposed. This alternative embodiment of the multi-layer test device 40 for analyzing the concentration of fructosamine in a liquid sample has one substantially planar support member 42 with a detection aperture 43 which supports a buffer layer pad 14 juxtaposed to, and in fluid communication with, an indicator layer pad 15.

The following examples are intended to illustrate but not limit the present invention.

EXAMPLE I

Preparation and Testing of a Two-Layer
Fructosamine Test Devices Having Varying
Concentrations of Indicator Buffer Layer Pad Cytosep® membrane #1661 (Ahlstrom Filtration, Inc., Mt. Holly Spring, Pa.) was placed for one minute in a 1.25 molar solution of guanidinium carbonate buffer (Sigma Chemical Co., St. Louis, Mo.) having a pH of 11.7. Excess buffer was removed and the membrane was dried for 30 minutes at 60° C. After drying, the buffer layer pad was stored in a desiccator cabinet until the buffer layer was ready for use in the multi-layer test device. When ready for use, a 7 mm circle buffer layer pad was prepared.

Indicator Layer Pad

Biodyne A nylon membranes (Pall Co., East Hills, N.Y.) of 5 µm pore size were placed in solutions containing varying concentrations from 1 to 30 millimolar of nitroblue tetrazolium chloride (NBT) (Sigma Chemical Co., St. Louis, Mo.) in water for one minute. Excess NBT was removed and the membranes were dried at 60° C. for 30 minutes. After drying, the impregnated membrane was stored in the absence of ambient light. When ready for use, a 7 mm circle NBT indicator layer pad was prepared.

Support Members

Two white plastic substantially planar strips were used (part # Diag 0001, Diagnostic Solutions, Inc., Irvine, Calif.). Each plastic strip had a hole of a size less than 7 mm, the top plastic strip with a sample aperture and the bottom strip with a detection aperture. Adhesive tape surrounds the holes on the inner sides of the plastic strips.

Multi-Layer Test Device

One of the above described buffer layer pads was superposed above one of the above described NBT indicator layer pads. The two superposed pads were sandwiched between two plastic strips such that the sample aperture exposed the buffer layer pad and the detection aperture exposed the NBT indicator layer pad.

Multi-Layer Test Device Analysis

Figure 5:
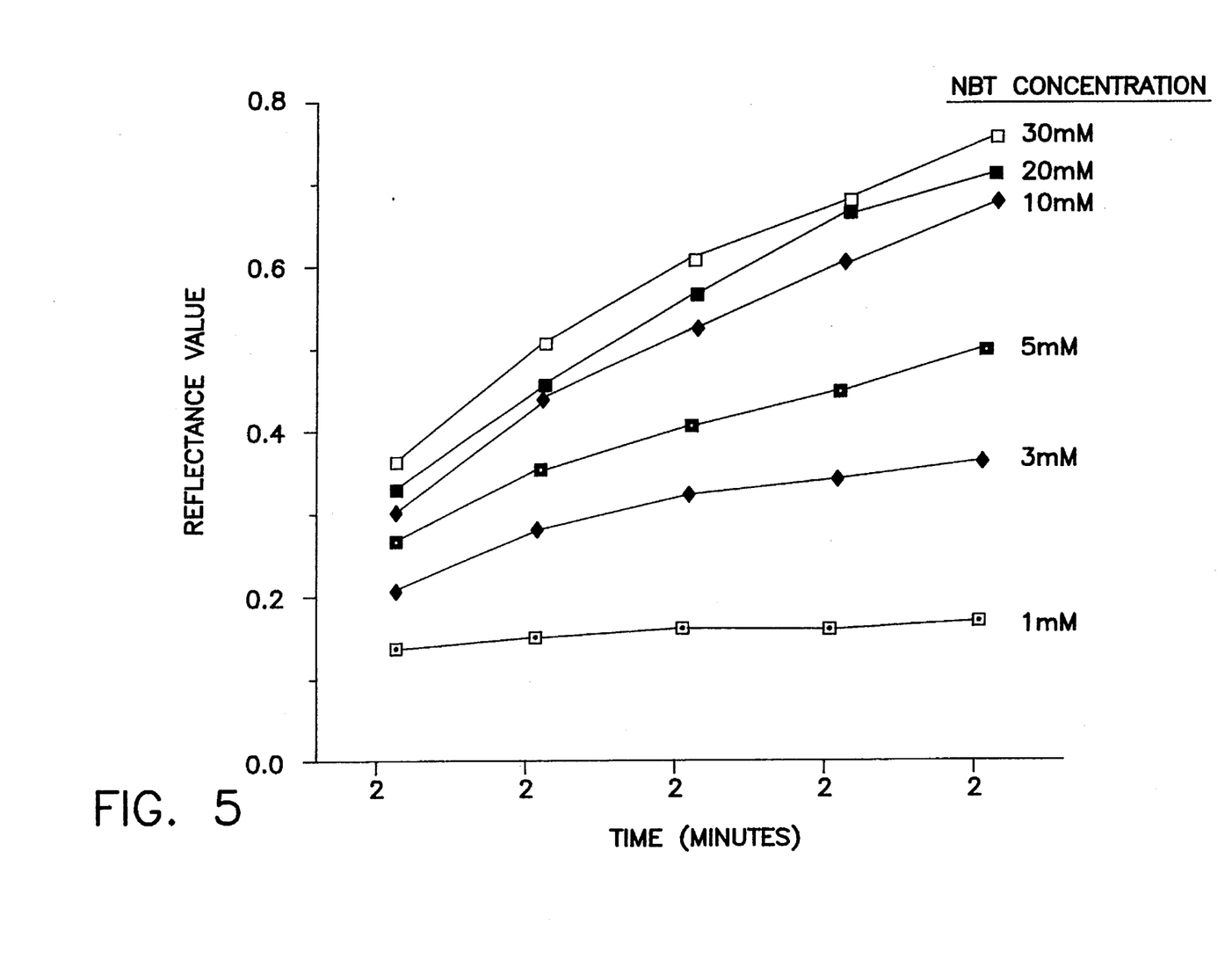
FIG. 5 graphs the test results of deoxymorpholino fructose (DMF) liquid samples added to multi-layer test devices prepared with varying concentrations of NBT.

10 µl samples of a 1 millimolar solution of deoxymorpholino fructose (DMF) (Sigma Chemical Co., St. Louis, Mo.) in water were applied at the sample aperture directly onto the buffer layer pad. The DMF liquid sample flowed through the buffer layer pad to the NBT buffer layer pad where the alkaline DMF reacted with the NBT dye to form a colored product. The magenta color was measured at 2, 4, 6, 8, and 10 minutes using a Gretag Reflectance Densitometer. The same protocol was repeated for concentrations from 1 to 30 millimolar NBT. FIG. 5 shows the color produced up to ten minutes after the addition of DMF to the multi-layer test devices prepared with the varying concentrations of NBT.

EXAMPLE II

Preparation of a Two-Layer Fructosamine Test
Devices and Testing of Serum-Based Fructosamine
Calibrators Test devices were prepared as in Example I above with the exception that the material used for the buffer layer pad was Non-woven Rayon S-5 (Schleicher and Schuell, Keene, N.H.) and the indicator layer pad was Loprodyne membrane (Pall Co., East Hills, N.Y.) impregnated with a 15 millimolar concentrated solution of NBT.

Multi-Layer Test Device Analysis

10 µl serum-based fructosamine calibrator samples (blank, normal, intermediate, and elevated) (Isolab, Inc., Akron, Ohio) were applied at the sample aperture directly onto the buffer layer pad. The serum-based liquid samples flowed through the buffer layer pad to the NBT buffer layer pad where the alkaline fructosamine reacted with the NBT dye to form a colored product. The magenta color was measured at 2, 4, 6, 8, and 10 minutes using a Gretag Reflectance Densitometer (Diagnostic Solutions, Inc., Irvine, Calif.). The multi-layer test device was able to accurately distinguish between the different serum-based fructosamine samples as indicated by the results given below.

|  | TIME | | | |
| --- | --- | --- | --- | --- |
| SAMPLE | 2' | 4' | 6' | 8' |
| Water (blank) | .20 | .22 | .23 | .25 |
| Normal calibrator | .26 | .29 | .33 | .35 |
| Intermediate calibrator | .30 | .37 | .44 | .48 |

-continued

| SAMPLE | TIME | | | |
|---|---|---|---|---|
| | 2' | 4' | 6' | 8' |
| Elevated Calibrator | .32 | .40 | .47 | .53 |

Although the invention has been described with reference to the disclosed embodiments, it should be understood that various modifications can be made without departing from the spirit of the invention. Accordingly, the invention is limited only by the following claims.

We claim:

1. A multi-layer test device for analyzing the concentration of fructosamine in a liquid sample, comprising:

a non-opaque, liquid permeable buffer layer containing a buffer having a pH value of at least 9;

an indicator layer containing an indicator capable of being reduced by fructosamine; and a support member optionally having a detection aperture; wherein the buffer layer is superposed above the indicator layer.

2. The multi-layer test device of claim 1 further comprising an additional support member having a sample aperture and wherein the buffer layer and the indicator layer are sandwiched between the support members.

3. The multi-layer test device according to claim 2 wherein the support members are substantially planar support members.

4. The multi-layer test device according to claim 1 further comprising one or more additional layers.

5. The multi-layer test device according to claim 4 wherein the additional layers are selected from the group consisting of a separation layer, a radiation blocking layer, an interference removal layer, a contamination prevention layer, a dialysis layer, a filtering layer, and a support layer.

6. The multi-layer test device according to claim 1 wherein the buffer has a pH value of between about 10 to about 12.

7. The multi-layer test device according to claim 1 wherein the indicator is selected from a group consisting of a chromogenic dye and a fluorescent reagent.

8. The multi-layer test device according to claim 7 wherein the indicator is a tetrazolium dye.

9. A multi-layer test device for analyzing the concentration of fructosamine in a liquid sample, comprising:

a buffer layer containing a buffer having a pH value of at least 9;

an indicator layer containing an indicator capable of being reduced by fructosamine; and a support member optionally having a detection aperture; wherein the buffer layer and the indicator layer are juxtaposed.

10. The multi-layer test device of claim 9 further comprising an additional support member having a sample aperture and wherein the buffer layer and the indicator layer are sandwiched between the support members.

11. The multi-layer test device according claim 10 wherein the support members are substantially planar support members.

12. The multi-layer test device according to claim 9 further comprising one or more additional layers.

13. The multi-layer test device according to claim 12 wherein the additional layers are selected from the group consisting of a separation layer, a radiation blocking layer, an interference removal layer, a contamination prevention layer, a dialysis layer, a filtering layer, and a support layer.

14. The multi-layer test device according to claim 9 wherein the buffer has a pH value of between about 10 to about 12.

15. The multi-layer test device according to claim 9 wherein the indicator is selected from a group consisting of a chromogenic dye and a fluorescent reagent.

16. The multi-layer test device according to claim 15 wherein the indicator is a tetrazolium dye.

17. A multi-layer test device for analyzing the concentration of fructosamine in a liquid sample, comprising:

a plastic first substantially planar support member having a sample aperture;

a plastic second substantially planar support member having a detection aperture;

a non-opaque, liquid permeable buffer layer containing a buffer having a pH value of between about 10 and about 12; and an indicator layer containing a nitroblue tetrazolium chloride dye, wherein the buffer layer is superposed above the indicator layer and wherein the buffer layer and indicator layer are sandwiched between the first support member and the second support member.

18. A method for analyzing the concentration of fructosamine in a liquid sample, comprising the steps of:

(a) providing a test device having a non-opaque, liquid permeable buffer layer containing a buffer having a pH value of at least 9, an indicator layer containing an indicator capable of being reduced by fructosamine, and a support member optionally having a detection aperture, wherein the buffer layer is superposed above the indicator layer;

(b) applying a liquid sample to the test device; and (c) analyzing the indicator layer for the concentration of fructosamine present in the liquid sample.

19. The method of claim 18 wherein the test device of step (a) further comprises an additional support member having a sample aperture and wherein the buffer layer and the indicator layer are sandwiched between the support members.

20. The method according to claim 18 wherein the concentration of fructosamine is analyzed on the indicator layer by visually or instrumentally determining the intensity or degree of color change or fluorescence.

21. The method of claim 18 wherein the analysis of step (c) is carried out at ambient temperature.

22. A method for analyzing the concentration of fructosamine in a liquid sample, comprising the steps of:

(a) providing a test device having a buffer layer containing a buffer having a pH value of at least 9, an indicator layer containing an indicator capable of being reduced by fructosamine, and a support member optionally having a detection aperture, wherein the buffer layer and the indicator layer are juxtaposed;

(b) applying a liquid sample to the test device; and (c) analyzing the indicator layer for the concentration of fructosamine present in the liquid sample.

23. The method of claim 22 wherein the test device of step (a) further comprises an additional support member having a sample aperture and wherein the buffer layer and the indicator layer are sandwiched between the support members.

24. The method according to claim 22 wherein the concentration of fructosamine is analyzed on the indicator layer by visually or instrumentally determining the intensity or degree of color change or fluorescence.

25. The method of claim 22 wherein the analysis of step (c) is carried out at ambient temperature.

* * * * *

UNITED STATES PATENT AND TRADEMARK OFFICE
CERTIFICATE OF CORRECTION

Page 1 of 2

PATENT NO. : 5,470,752
DATED : November 28, 1995
INVENTOR(S) : Burd et al.

It is certified that error appears in the above-indentified patent and that said Letters Patent is hereby corrected as shown below:

Drawings: Delete Fig. 5, and substitute therefor the Fig. 5, on the attached sheet.

In column 6, line 50, please delete "piper" and replace therefor with --pipet--.

Signed and Sealed this

Nineteenth Day of November, 1996

Attest:

BRUCE LEHMAN

Attesting Officer  Commissioner of Patents and Trademarks

UNITED STATES PATENT AND TRADEMARK OFFICE
CERTIFICATE OF CORRECTION

PATENT NO. : 5,470,752

DATED : Nov. 28, 1995

INVENTOR(S) : Burd et al.

It is certified that error appears in the above-identified patent and that said Letters Patent is hereby corrected as shown below:

FIG. 5